(12) United States Patent
Bannister et al.

(10) Patent No.: US 6,184,004 B1
(45) Date of Patent: Feb. 6, 2001

(54) PROCESS FOR THE PREPARATION OF GALANTHAMINE AND ITS DERIVATIVES

(75) Inventors: Robin Mark Bannister; Raymond McCague, both of Cambridge (GB)

(73) Assignee: Janssen Pharmaceutica, N.V. (BE)

( * ) Notice: Under 35 U.S.C. 154(b), the term of this patent shall be extended for 0 days.

(21) Appl. No.: 09/043,598

(22) PCT Filed: Sep. 23, 1996

(86) PCT No.: PCT/GB96/02335

§ 371 Date: May 26, 1998

§ 102(e) Date: May 26, 1998

(87) PCT Pub. No.: WO97/11078

PCT Pub. Date: Mar. 27, 1997

(30) Foreign Application Priority Data

Sep. 21, 1995 (GB) .................................................. 9519268

(51) Int. Cl.$^7$ ........................ C12P 17/18; C07D 491/08; A61K 35/78
(52) U.S. Cl. ...................... 435/119; 514/80; 514/215; 540/581; 540/576; 424/195.1
(58) Field of Search ...................... 424/195.1; 514/80, 514/215; 540/576, 581; 435/119

(56) References Cited

U.S. PATENT DOCUMENTS 4,290,862 * 9/1981 Vlahov et al. ........................ 205/424
5,428,159 * 6/1995 Shieh et al. ........................... 540/581
5,633,238 * 5/1997 Snorrason ............................... 514/80

OTHER PUBLICATIONS

Szewczyk et al. J. Heterocyclic Chem. vol. 25, pp. 1809–1811, 1988.*
Szewczyk et al. J. Heterocyclic Chem. vol. 32, pp. 195–199, 1995.*
Kutbay et al. Turkish J. Bot. vol. 17(1), pp. 1–4, abstract enclosed, 1993.*
Propavko, S. Apicult. Abstract, vol. 21(3), p. 127, 1970.*
Yang et al. J. Chin. Chem. Soc. vol. 15(3), pp. 97–105, abstract enclosed, 1968.*
Fuganti, C. La Chimica e L'Industria, vol. 51 (11), p. 1254, 1969.*
Hawley, G. Condensed Chemical Dictionary, 8th ed., p. 907, 1971.*

* cited by examiner

*Primary Examiner*—Christopher Tate
(74) *Attorney, Agent, or Firm*—Saliwanchik, Lloyd & Saliwanchik

(57) ABSTRACT

The subject invention pertains to a process for preparing a compound having a formula (4) or (5), in either optically-enriched or racemic form, wherein $R^1$, $R^2$, $R^3$ and $R^4$ are independently selected from hydrogen, alkyl, aryl, alkaryl, aralkyl and acyl groups. In one embodiment, the process of the invention comprises mixing with a plant extract obtained from crushed daffodil bulbs or crushed snowdrop bulbs an oxidative cyclisation precursor of the compound.

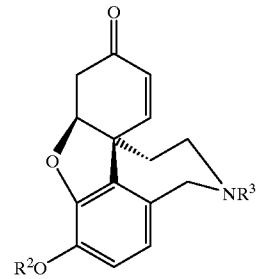

(4)

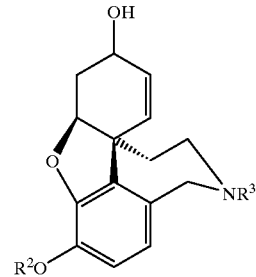

(5)

7 Claims, No Drawings

PROCESS FOR THE PREPARATION OF GALANTHAMINE AND ITS DERIVATIVES

FIELD OF THE INVENTION

The present invention relates to a process for producing galanthamine and/or its derivatives from plant extracts.

BACKGROUND OF THE INVENTION

Galanthamine (and its derivatives) are useful compounds for the treatment of Alzheimer's disease and related illnesses. Currently galanthamine, nor-galanthamine and the oxidised precursors thereof, narwedine and nor-narwedine, are usually obtained by extraction from particular types of bulbs, such as daffodils or snowdrops. The yields of these extractive procedures are extremely low, resulting in product (s) which are expensive and in short supply.

Studies have shown that the biosynthesis of such compounds probably proceeds by a pathway similar to that shown in Scheme 1 below, where the key step is an oxidative cyclisation. These studies have also indicated that when the cyclisation precursor lacks a methyl group on the amine nitrogen (i.e. R=H) the biosynthesis to narwedine and galanthamine is disfavoured, and instead proceeds down other pathways, e.g. to pyrrolo(de)phenanthridine and ethanophenanthridine alkaloids (see Barton and Kirby, J. Chem. Soc. (1961) 806 and Fuganti et al, Tetrahedron Lett. (1974) 2261).

SUMMARY OF THE INVENTION

According to the present invention, a process for preparing a compound having a formula (4) or (5), in either optically-enriched or racemic form, wherein $R^1$, $R^2$, $R^3$ and $R^4$ are independently selected from hydrogen, alkyl, aryl, alkaryl, aralkyl and acyl groups, comprises mixing with a plant extract an oxidative cyclisation precursor of the said compound. All formulae are depicted below.

Surprisingly, the process of the present invention is capable of achieving higher yields of the desired compounds than simple extraction from bulbs, and has the further advantage of its own simplicity. The process is particularly useful for the preparation of such compounds in optically-enriched form, more particularly (−)-galanthamine or (−)-narwedine.

DESCRIPTION OF THE INVENTION

Whether the process of the invention results in an optically-enriched or racemic form of a desired compound may depend upon the choice of the precursor to be mixed with the plant extract. Typically, however, an optically-enriched form is achieved. This is particularly advantageous when the product is (−)-galanthamine, or a derivative thereof, on account of its therapeutic activity. However, if the product is racemic or optically-enriched narwedine, or a derivative thereof, it can be readily converted to optically-enriched, eg. (−), galanthamine by a process such as that described by Shieh et al, J. Org. Chem. (1994) 59: 5463.

By optically-enriched typically we mean mixtures of enantiomers having an enantiomeric excess of at least 50%, and more typically at least 80%, or 90% or higher, thereby including single enantiomer form.

The groups $R^1$ to $R^4$ have been defined above, and typically include up to 20 carbon atoms. The preferred precursor compound for the preparation of (−)-galanthamine has surprisingly been found to be a secondary amine having the formula (3), below, in which the nitrogen atom is unsubstituted, ie. $R^3$=H, contrary to what is disclosed in the prior art discussed above. Particularly preferred precursor compounds are of formula (3) in which $R^1$=$R^3$=$R^4$=H and $R^2$=alkyl, preferably methyl.

The plant extract is typically derived from daffodils or snowdrops, although other plants may give suitable extracts, and is preferably derived from the bulb of the plant. The extract is typically used in fragmented form, for instance by crushing with a pestle and mortar, and is then suspended in a liquid medium. Typically, the liquid medium comprises an aqueous buffer, optionally including an additive such as an organic solvent or a surfactant. The precursor compound is then added to the liquid mixture, and preferably stirred for a period. The mixture is then extracted in a conventional manner.

The present invention is now further illustrated by the following Example.

EXAMPLE

Daffodil bulbs which had been stored in a refrigerator were allowed to warm to room temperature over night. The bulbs were crushed with a pestle and mortar and a 1 g sample of this material was stirred with 10 mg of a secondary amine of formula (3) below, in which $R^1$=$R^3$=$R^4$=H and $R^2$=Me, in aqueous phosphate buffer (20 ml) and ethanol (10 ml) for 18 hours. The mixture was then extracted with ethyl acetate and then concentrated in vacuo. Gas chromatographic analysis of the residue indicated that three times the amount of (−)-galanthamine was produced in comparison with a control reaction, which was run under identical conditions but without the addition of the amine (3).

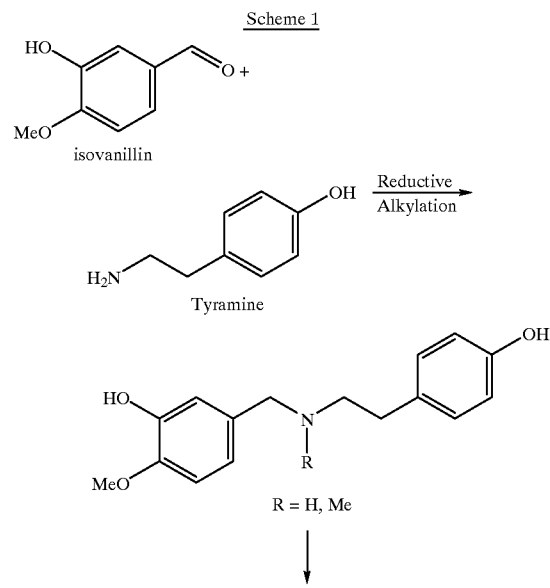

Scheme 1

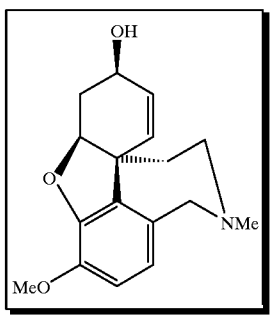

(−)-Galanthamine

Formulae (1)
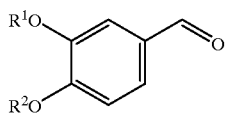

(2)
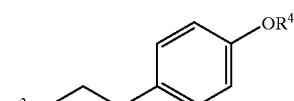

(3)
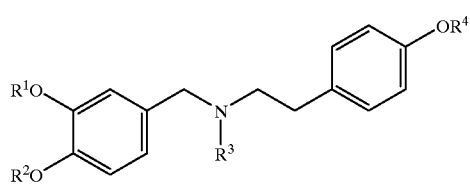

(4)
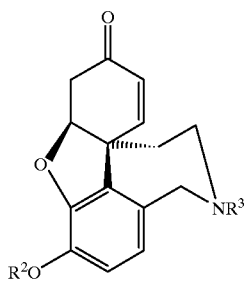

(5)
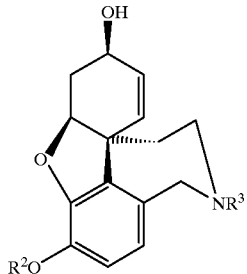

What is claimed is:

1. A process for producing a compound having a formula (4) or (5)

(4)
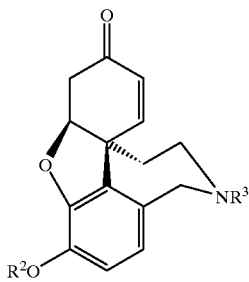

(5)
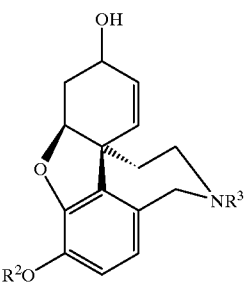

comprising:
a) mixing an effective amount of a crude plant extract obtained from crushed daffodil bulbs or crushed snowdrop bulbs with an effective amount of an amine having a formula (3)

(3)
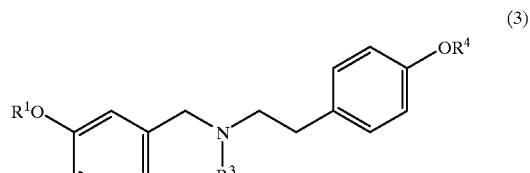

in a suitable liquid medium for a sufficient time to produce said compound, and
b) recovering said compound,
wherein $R^1$, $R^2$, $R^3$, and $R^4$ are independently selected from the group consisting of hydrogen, alkyl, aryl, alkaryl, aralkyl, and acyl groups.

2. The process according to claim 1, wherein the amine of formula (3) is prepared by mixing the compounds of formula (1) and formula (2)

(1)
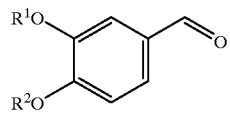

(2)
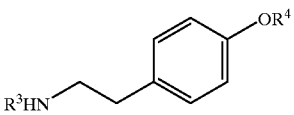

wherein $R^1$, $R^2$, $R^3$ and $R^4$ are as defined in claim 1.

3. The process according to claim 1, wherein said compound is prepared in optically-enriched form.

4. The process according to claim 3, wherein said compound prepared is (−)-galanthamine.

5. The process according to claim 4, wherein the amine of formula (3) has $R^3$=H.

6. The process according to claim 5, wherein in the amine of formula (3) $R^1$=$R^4$=H and $R^2$=alkyl.

7. The process according to claim 6, wherein $R^2$=methyl.

* * * * *